United States Patent
Cunkle et al.

(10) Patent No.: US 7,312,332 B2
(45) Date of Patent: Dec. 25, 2007

(54) CHLOROHYDRIN AND CATIONIC COMPOUNDS HAVING HIGH AFFINITY FOR PULP OR PAPER

(75) Inventors: Glen T. Cunkle, Stamford, CT (US); David Devore, Nyack, NY (US); Thomas F. Thompson, Highland Mills, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 353 days.

(21) Appl. No.: 10/978,673

(22) Filed: Nov. 1, 2004

(65) Prior Publication Data

US 2005/0092452 A1   May 5, 2005

Related U.S. Application Data

(63) Continuation of application No. 09/658,924, filed on Sep. 11, 2000, now Pat. No. 6,989,449.

(60) Provisional application No. 60/154,112, filed on Sep. 15, 1999.

(51) Int. Cl.
*C07D 471/10* (2006.01)
*C07D 471/02* (2006.01)

(52) U.S. Cl. .......................... 546/20; 546/19

(58) Field of Classification Search ................ 546/20, 546/19
See application file for complete search history.

(56) References Cited

U.S. PATENT DOCUMENTS

| 3,755,586 A | | 8/1973 | Sanzari et al. ............ 424/267 |
| 4,219,465 A | * | 8/1980 | Soma et al. ............... 524/102 |
| 5,457,204 A | | 10/1995 | Steinmann ................ 546/242 |
| 6,254,724 B1 | | 7/2001 | Seltzer et al. ............. 162/70 |

FOREIGN PATENT DOCUMENTS

| CA | 2164394 | 6/1996 |
| EP | 0006536 | 1/1980 |
| EP | 0309401 | 3/1989 |
| WO | 97/36041 | 10/1997 |
| WO | 99/05108 | 2/1999 |

OTHER PUBLICATIONS

I. E. Arakin et al., Khimiya drevesiny (Chemistry of Wood), 1982, No. 2, 114.
A. D. Sergeev et al., Khimiya drevesiny (Chemistry of Wood), 1984, No. 5, pp. 20-22.
V. I. Khodyrev et al., Vysokomol soyed, A29, No. 3, pp. 616-621 (1987) [Polymer Sci. U.S.S.R., 29, No. 3, 688-694, (1987)].
M-K. Sykr et al., J. Assoc. of Paper and Pulp Tech., 29, pp. 135-140 (1990).
P. Fornier de Violet et al., Cellulose Chem. Tech., 24, pp. 225-235 (1990).
R. Agnerno et al., Appita, 6$^{th}$ International Symposium on Wood and Pulping Chemistry, vol. 1 (1991).
S. Omori et al., J. Assoc.. Paper and Pulp Tech., 48, pp. 1388-1394 (1993).
M. Paulsson et al., The 8$^{th}$ International Symposium on Wood and Pulping Chemistry, vol. III, pp. 61-66 (1995).
Z-H. Wu et al., Holzforschung, 48, (1994), pp. 400-404.
C. Heitner, Chemistry of Brightness Reversion and Its Control, Chapter 5, TAPPI, Atlanta, 1996, pp. 183-212.
C. Heitner et al., ACS Symposium Series 531, Photochemistry of Lignocellulosic Materials, (1993), pp. 1-25.
Chemical Abstract I I I :209083 for M. Klein et al., J. Pharmacol. Exp. Ther., vol. 251, No. 1, (1989), pp. 207-215.
Chemical Abstract 128:61939 for JP 9302026 (1997).

* cited by examiner

*Primary Examiner*—Charanjit S. Aulakh
(74) *Attorney, Agent, or Firm*—Shiela A. Loggins

(57) ABSTRACT

Selected chlorohydrin and cationic compounds containing nitroxide or hydroxylamine moieties are effective in stabilizing pulp or paper, especially pulp or paper containing lignin, against yellowing and discoloration due to the adverse effects of light. These compounds are added at various points in the paper-making process, especially at the wet ends, making the need for water soluble or water dispersible materials having high affinity for pulp or paper essential. This performance is often further enhanced by the presence of one or more coadditives selected from the group consisting of the UV absorbers, the polymeric inhibitors, the nitrones, the fluorescent whitening agents and metal chelating agents. Combinations of hydroxylamines or their salts, benzotriazole or benzophenone UV absorbers and a metal chelating agent are particularly effective.

5 Claims, No Drawings

CHLOROHYDRIN AND CATIONIC COMPOUNDS HAVING HIGH AFFINITY FOR PULP OR PAPER

This is a continuation of application Ser. No. 09/658,924, filed Sep. 11, 2000, now U.S. Pat. No. 6,989,449 which claims benefit under 35 USC 119(e) of provisional application No. 60/154,112, filed Sep. 15, 1999.

The instant invention pertains to new chlorohydrin or cationic compounds having nitroxide or hydroxylamine moieties which have high affinity for pulp or paper, particularly that containing lignin, and which compounds are useful in preventing the loss of brightness and for enhancing resistance to yellowing in pulp or paper, especially that which still contains lignin. This performance is often further enhanced by the presence of one or more coadditives selected from the group consisting of the UV absorbers, the polymeric inhibitors, the nitrones, the fluorescent whitening agents and metal chelating agents. Combinations of hydroxylamines or their salts, benzotriazole or benzophenone UV absorbers and a metal chelating agent are particularly effective.

BACKGROUND OF THE INVENTION

High-yield and ultra-high yield wood pulps undergo rapid light-induced discoloration, particularly when they are exposed to near ultraviolet light (wave lengths 300-400 nm) in indoor fluorescent light and daylight. This characteristic restricts their use to short-life, low-value paper products. High-yield and ultra-high yield wood pulps can be bleached to a high level of whiteness. If this whiteness could be stabilized against discoloration, these bleached high-yield pulps could displace significant amounts of more expensive fully-bleached, low-yield chemical pulps.

This discoloration is ascribed to the substantial lignin content of high-yield pulps totally about 20-45% by mass. Phenoxy radicals are the key intermediates in the reaction mechanism. Several light-induced reactions have been proposed to account for their formation such as cleavage of the aryl ether bond of phenacyl aryl ether groups, or breakdown of ketyl radicals formed from saturated aryl-glycerol β-aryl ether structures in lignin. The phenoxy radicals are oxidized by other oxygen-centered radicals (alkoxy and perhydroxy) to form yellow chromophores. (C. Heitner, "Photochemistry of Lignocellulosic Materials", C. Heitner, J. C. Scaiano, Eds.; ACS Sym. Ser. 531, 1-25 (1993).)

I. E. Arakin et al., Khymiya drevesiny (Chemistry of Wood), 1982. No. 2, 114 and A. D. Sergeev et al., ibid, 1984, No. 5, 20 disclosed that the use of iminoxyl radicals such as TEMPO (1-oxyl-2,2,6,6-tetramethylpipedidine) is useful in the delignification of wood using the one-stage oxygen-soda (alkaline) process, but made no mention or suggestion of any activity provided by TEMPO on preventing light-induced discoloration of paper or pulp made from such treated wood.

EP 717,143 and WO 97/36041 describe a multicomponent system for changing, reducing or bleaching lignin and lignin-containing materials which comprise an oxidation catalyst, and an N-hydroxyl mediator compound such as N-hydroxyphthalimide or a dialkyl-hydroxylamine. These references are aimed at the delignificabon of wood. There is no mention or suggest of any activity provided by the N-hydroxyl compounds in preventing the light-induced discoloration of paper or pulp made from such treated wood.

V. I. Khodyrev et al., Vysokomol soyed, A29. No. 3, 616 (1987) [Polymer Sci. U.S.S.R., 29 No. 3, 688 (1987)] show that the photoinitiated oxidation by oxygen causes weathering of cellulosic textile materials such as flax or cotton, and that the light stability of the cellulose could be improved by photostabilizers such as the UV absorbers, benzophenols and 1-oxyl-2,2,6,6-tetramethyl-4-hydroxypiperidine. The UV absorbers offer no protection, and are actually detrimental. The authors noted that the stable nitroxyl radical interacts with alkyl radicals in the cellulose to afford its salubrious stabilizing activity. There is no suggestion by the authors that this stabilizing activity could be applied successfully in wood pulp and/or paper made therefrom.

M-K. Syler et al., J. Assn. Paper Pulp Tech, 29, 135 (1990) show that selected metal salts such as magnesium sulfate and lower alkanoic acids inhibit color reversion in bleached pulp.

P. Fomier de Violet et al., Cellulose Chem. Tech., 24, 225 (1990) show that the use of UV absorbers and hydrogen donor agents such as thiols, ascorbic acid, etc. help prevent the photoinduced discoloration of hydrogen peroxide bleached wood pulp, but that chain breakers such as hindered phenols and hindered amines (having >N—H or >N—CH$_2$-moieties) had no or even a detrimental effect on preventing photoinduced discoloration.

R. Agnemo et al., 6th International Symposium on Wood and Pulping Chemistry, Appita, 1991, confirmed that free hydroxyl radicals plus lignin lead to undesirable photoyellowing in pulp and paper.

S. Omori et al., J. Assn. Paper Pulp Tech, 48, 1388 (1993) describes the effect of antioxidants and UV absorbers on light reversion and concludes that the combination of an antioxidant and UV absorber prevents color reversion and has a synergistic effect in that activity.

M. Paulsson et al., 8th International Symposium Wood and Pulping Chemistry, Helsinki, 1995, show that efficient photostabilization of unbleached paper or hydrogen peroxide bleached TMP pulp can be achieved by acetylation.

There have been a number of different approaches proposed to inhibiting the yellowing of mechanical pulps. These include: radical scavengers and antoxidants; UV screens; elimination of chromophores after their formation; chemical modification of lignin by alkylation or acetylation; polymeric inhibitors; and two types of coadditives used in combination. Z-H. Wu et al., Holzforschung, 48, (1994), 400 discuss the use of radical scavengers like phenyl-N-tert-butylnitrone to reduce the formation of chromophores during mechanical pulping and give a more light-stable pulp.

C. Heitner, "Chemistry of Brightness Reversion and It Control, Chapter 5", in Pulp Bleaching-Principles and Practice, C. W. Dence, D. W. Reeve, Eds., TAPPI, Atlanta, 1996, pp 183-211, summarizes the state of the art in the thermal and light-induced yellowing of lignin-containing pulps such as thermomechanical (TMP) and chemithermomechical (CTMP) pulps, showing the seriousness of these undesirable effects discusses generally the then current prior art methods used to attack this problem. These include bleaching, the use of phosphites, UV absorbers, polyalkylene glycols and free radical scavengers such as ascorbic acid, thiols, thioethers, dienes and aliphatic aldehydes and chelating agents such as ethylenediaminetetra-acetic acid (EDTA). The author concluded that, although much progress had been made, much still remains to be done before a successful and practical solution to this loss of brightness and undesirable yellowing of lignin-containing pulp and/or paper is found.

Copending applications Ser. Nos. 09/119,567; 09/234,253; 60/116,687 and 60/116,688 describe potential solutions where the use of selected hindered amine nitroxides, hindered amine hydroxylamines, N,N-dialkylhydroxyamines or their salts in combination with selected UV absorbers and metal chelating agents is seen to prevent loss of brightness and to enhance resistance to yellowing in mechanical or chemical pulp or paper, particularly mechanical pulp or paper still containing significant amounts of lignin.

DETAILED DESCRIPTION OF THE INVENTION

This invention involves novel chlorohydrin or cationic nitroxides, hydroxylamines or hydroxylamine salts which are water compatible and have high affinity for pulp. These compounds, when applied to pulp which still contains lignin, either chemical (kraft) pulp containing little lignin or particularly mechanical pulp containing significant amounts of lignin, either alone or in combination with UV absorbers, metal chelating agents, fluorescent whitening agents, sulfur containing inhibitors, phosphorus containing compounds, nitrones, benzofuran-2-ones and/or stabilizing polymers effectively confers light and thermal stability which is similar to that found in papers made from kraft pulp.

More particularly, the instant compounds are those of formulas I to X, or IA to XA

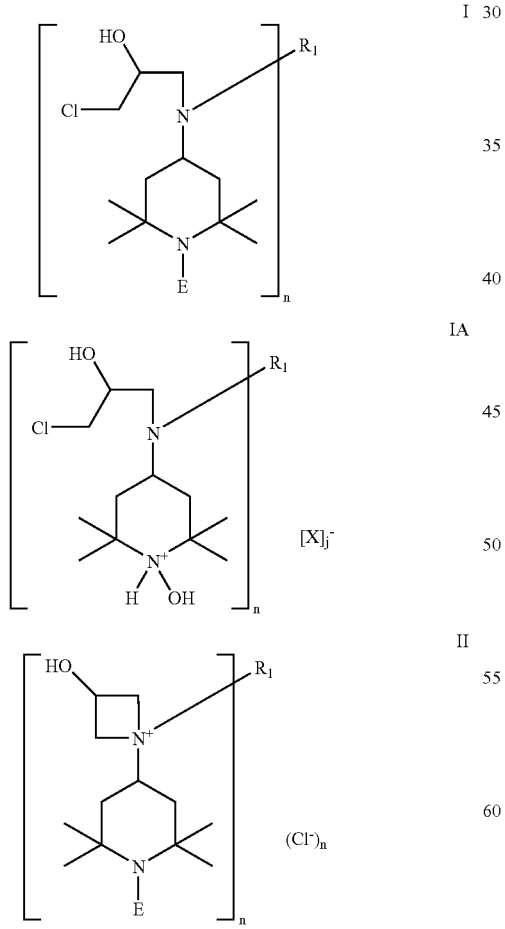

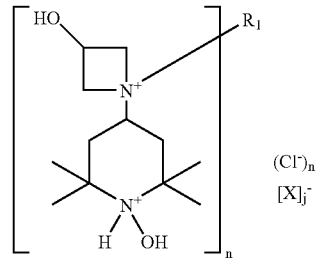

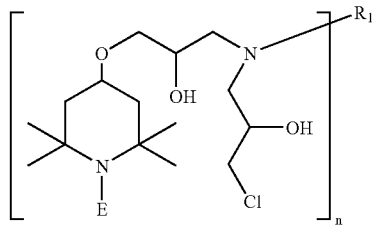

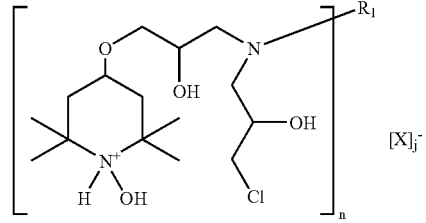

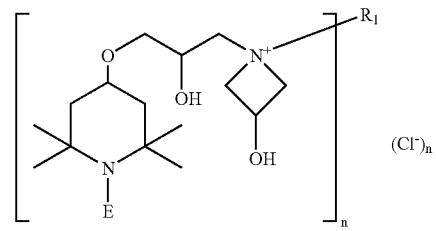

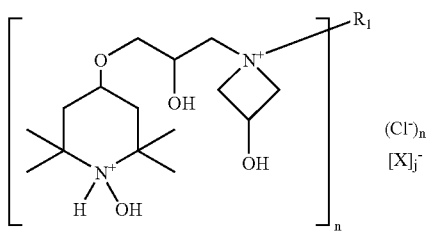

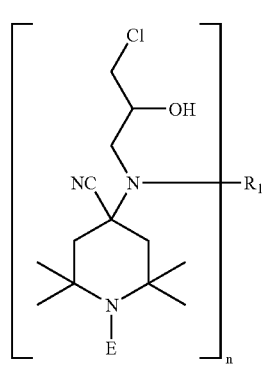

-continued
VA
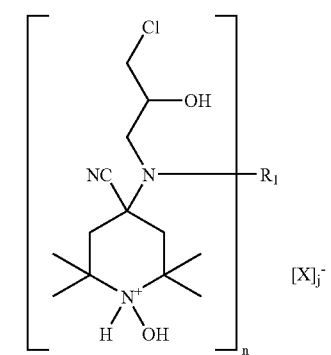
VI
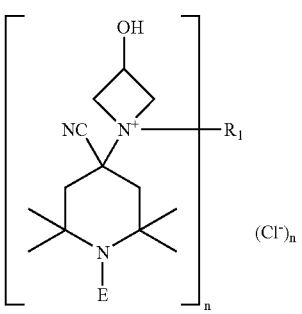
VIA
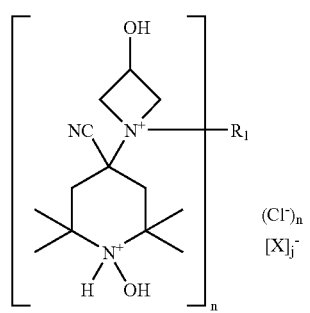
VII
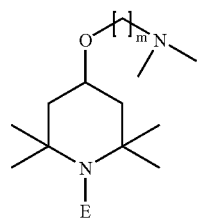
VIIA
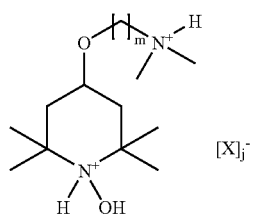
-continued
VIII
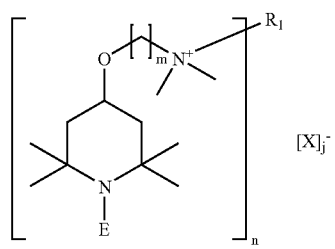
VIIIA
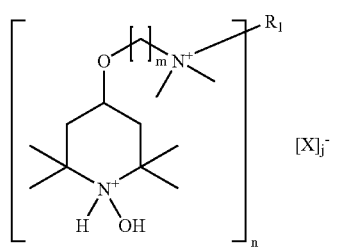
IX
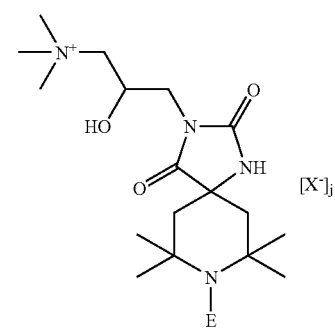
IXA
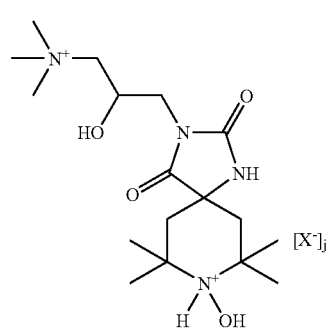
X
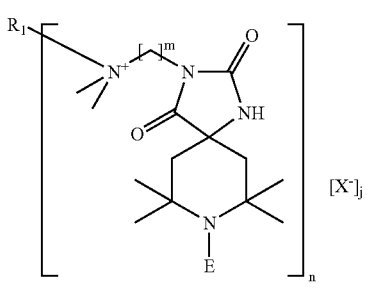

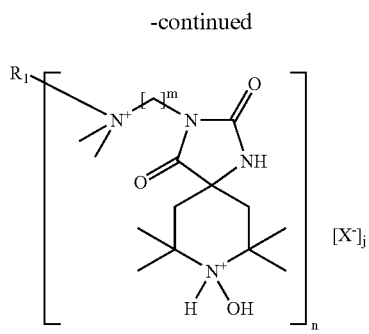  XA
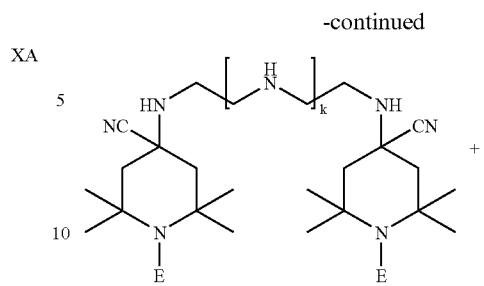  XII
or a product of one of the following reactions XI to XVI or XIA or XVIA
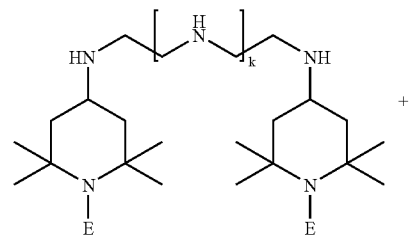  XI
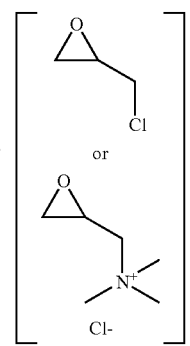
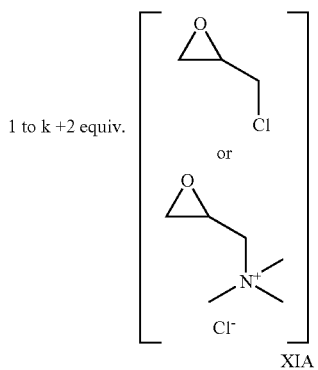
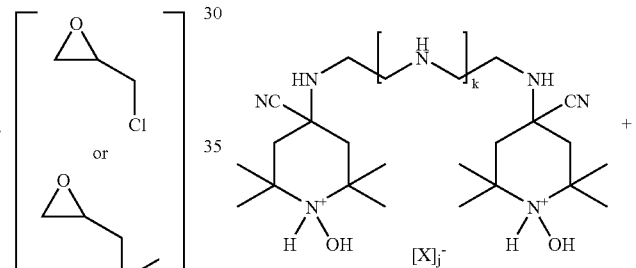  XIIA
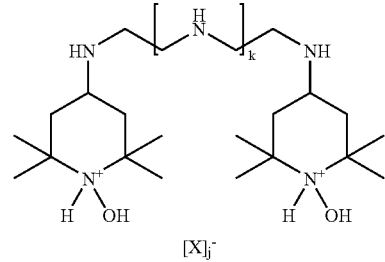  XIA
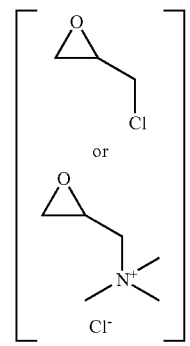
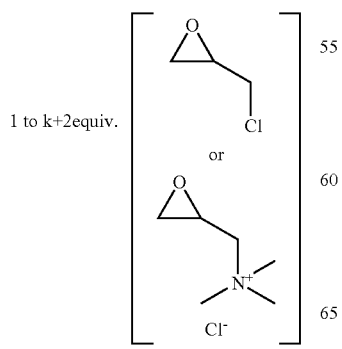
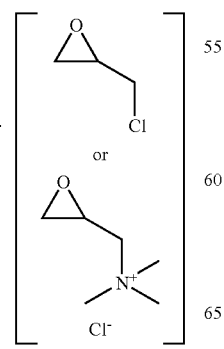
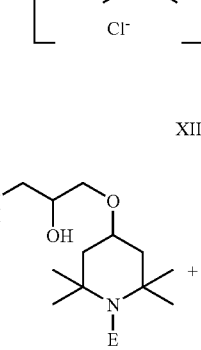  XIII

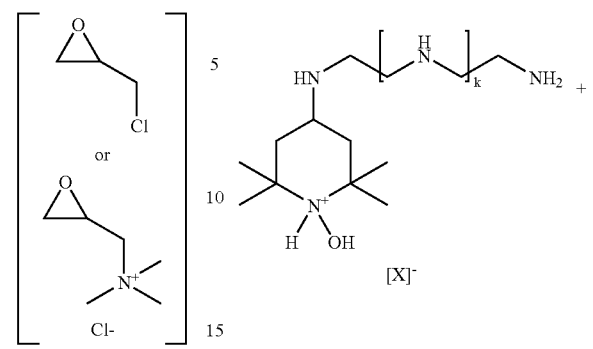
XIIIA
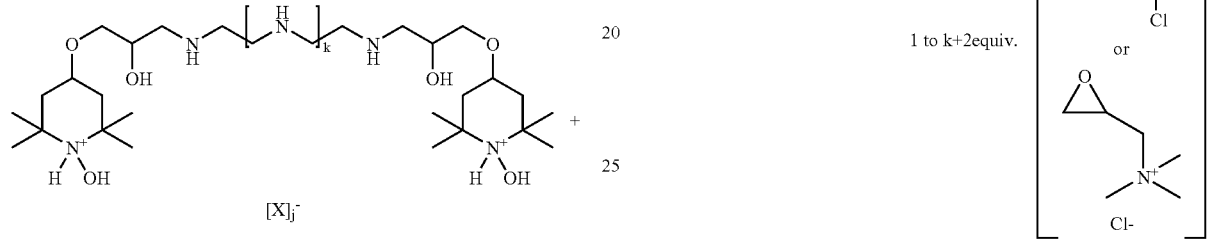
XIV
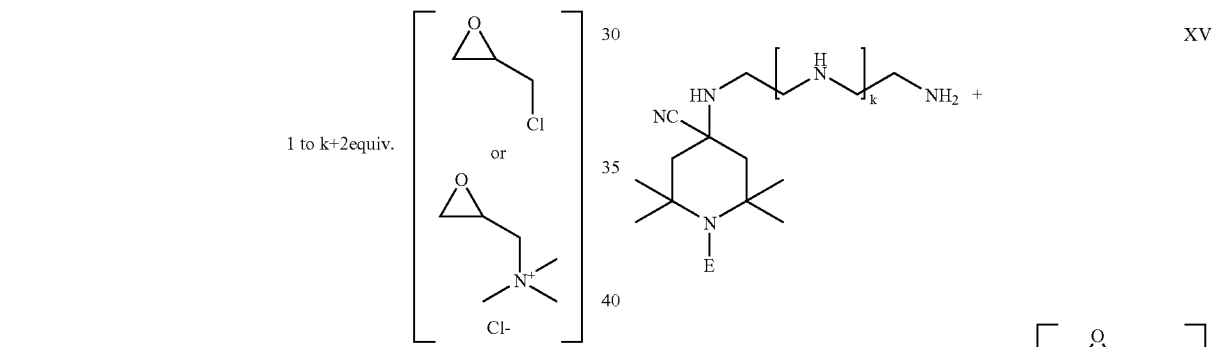
XIVA
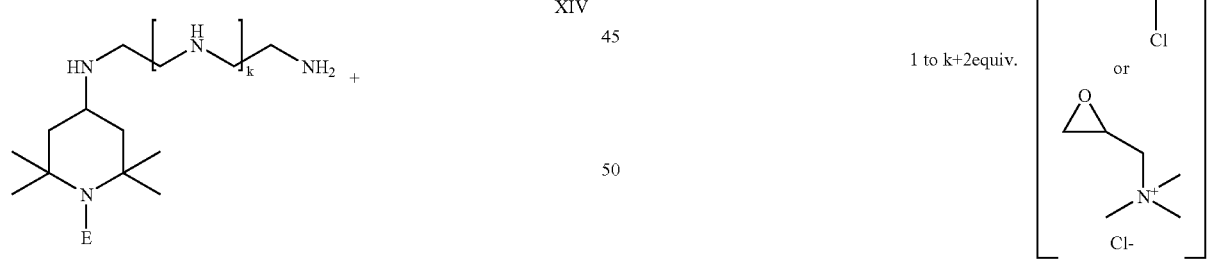
XV
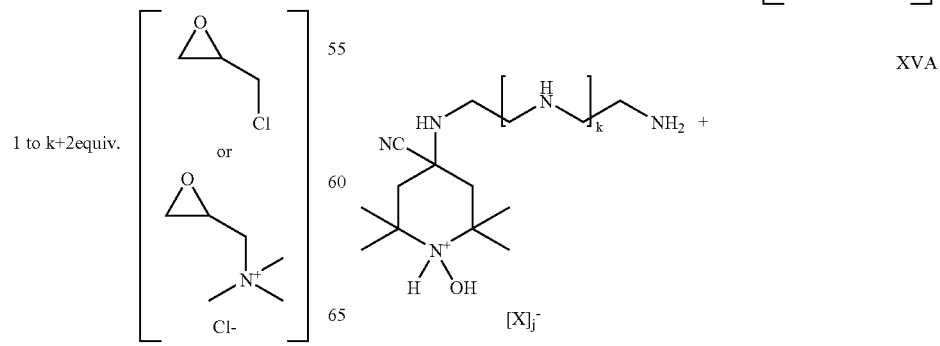
XVA

-continued 1 to k+2equiv. 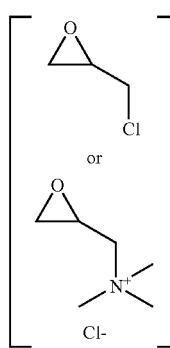

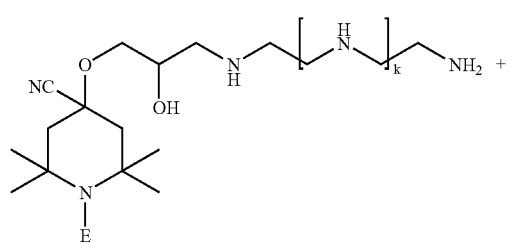

XVI 1 to k+2equiv. 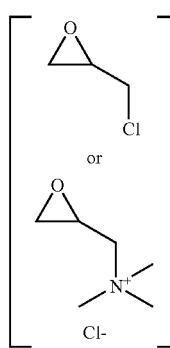

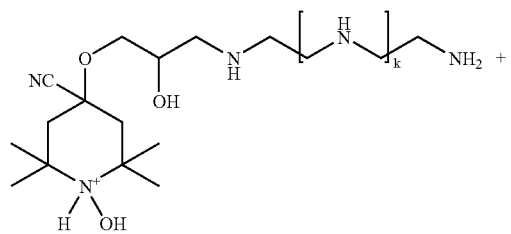

[X]$_j^-$

XVIA 1 to k+2equiv. 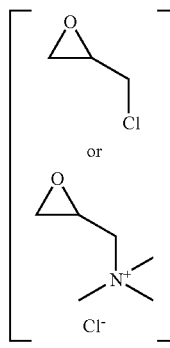

where k ranges from 1 to 10; n is 1 or 2; and m ranges from 2 to 6;

E is oxyl, hydroxyl, hydrogen, alkyl, alkyl substituted by hydroxyl, by oxo or by carboxy, alkyl interrupted by oxygen, by —COO— or by —OCO—, alkenyl, alkynyl, cycloalkyl, cycloalkenyl, bicycloalkyl, alkoxy, alkoxy substituted by hydroxyl, by oxo or by carboxy, alkoxy interrupted by oxygen, by —COO— or by —OCO—, cycloalkoxy, alkenyloxy, cycloalkenyloxy, aralkyl, aralkoxy, acyl, RCO0—, ROCOO—, RNCOO— or chloro where R is an aliphatic or aromatic moiety, when n is 1, $R_1$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, alkyl of 2 to 50 carbon atoms substituted by one to ten hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$^{n+}$(R$_2$)$_4$ where $R_2$ is hydrogen, alkyl of 1 to 8 carbon atoms or benzyl, or when n is 2, $R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, X is an inorganic or organic anion, where the total charge of cations is equal to the total charge of anions.

The index j determines the number of cations X necessary, together with other cations described in the above formulas such as Cl—, to equal the total charge of anions. Thus, in formulae I to VIA, j equals n divided by the valency of X, and in formulae VIIA to XVIA j equals the number of ammonium ions in the formula divided by the valency of X.

The instant stabilizers are conveniently obtained by reacting sterically hindered amine educts with suitable reactants known in the art. Reactions are carried out according to or in analogy to methods known in the art and illustrated in present examples. Suitable piperidine educts, e.g. carrying in 4-position an oxo, hydroxy, amino or carboxy group, are known compounds. For example, 1-oxyl-2,2,6,6-tetramethylpiperidin-4-one, 1-oxyl-2,2,6,6,-tetramethyl-4-hydroxypiperidine, 1-oxyl-2,2,6,6-tetramethyl-4-aminopiperidine and 1-oxyl-2,2,6,6-tetramethyl-4-carboxy-piperidine are known compounds and can be obtained commercially (Aldrich Chemical Company).

The above hydroxypiperidylammonium compounds indicated with the letter A (formulae IA, IIA, IIIA, IVA, VA, VIA, VIIA, VIIIA, IXA, XA, XIA, XIIA, XIIIA, XIVA, XVA, XVIA) are addition salts of the corresponding compound of the same number, without letter A, wherein E is OH, with an acid H$_{1/j}$X which may conveniently be prepared from these components or, as an alternative, from the corresponding hydroxypipeddylammonium compound with suitable reactands as described.

Preferably, X is phosphate, phosphonate, carbonate, bicarbonate, nitrate, chloride, bromide, iodide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylene-triaminepentaacetic acid, a diethylenediaminetetraacetic acid or of diethylenetriaminepenta-acetic acid, an alkylsulfonate or an arylsulfonate.

More preferred X are chloride, bromide, citrate, iodide or methylsulfate; especially preferred are chloride and bromide.

E is preferably oxyl, hydroxyl, alkoxy, alkoxy substituted by hydroxyl, oxo or carboxy or interrupted by oxygen or carboxy, cycloalkoxy, alkenyloxy, cycloalkenyloxy, aralkyl, aralkoxy, acyl, R(C=O)O—, RO(C=O)O—, RN(C=O)O— or chloro, where R is an aliphatic or aromatic moiety.

More preferably, E is oxyl, hydroxyl, $C_1$-$C_{18}$alkoxy; $C_3$-$C_{18}$alkoxy substituted by hydroxyl, oxo or carboxy or interrupted by oxygen or carboxy; $C_5$-$C_{12}$cycloalkoxy; $C_3$-$C_{12}$alkenyloxy; cyclohexenyloxy; aralkyl or aralkoxy of 7 to 15 carbon atoms; $C_1$-$C_{12}$acyl; R(C=O)O—, RO(C=O)O—, RN(C=O)O—, where R is $C_1$-$C_{18}$alkyl, phenyl, $C_7$-$C_{15}$ phenylalkyl, cyclohexyl, $C_2$-$C_3$alkenyl. Most preferred E is oxyl, hydroxyl, $C_1$-$C_8$alkoxy or cyclohexyloxy, especially oxyl or hydroxyl.

Any alkyl group within these definitions are preferably $C_1$-$C_{18}$alkyl comprising methyl, ethyl, propyl such as n- or isopropyl, butyl such as n-, iso-, sec- and tert-butyl, pentyl, hexyl, heptyl, octyl, nonyl, decyl, undecyl, dodecyl, tridecyl, tetradecyl, pentadecyl, hexadecyl, heptadecyl or octadecyl. Alkoxy is O-alkyl, preferably $C_1$-$C_8$alkoxy. Cycloalkyl usually is $C_5$-$C_{12}$cycloalkyl, preferably cyclohexyl. Alkenyloxy is usually $C_3$-$C_{12}$alkenyloxy, especially allyloxy. Aralkyl and aralkoxy usually is of 7 to 15 carbon atoms and is preferably $C_7$-$C_{15}$phenylalkyl or $C_7$-$C_{15}$phenylalkoxy. Acyl is preferably $C_1$-$C_{12}$alkyl-CO, especially acetyl, $C_2$-$C_3$alkenyl-CO, benzoyl. R as an aliphatic or aromatic moiety is preferably $C_1$-$C_{18}$alkyl, phenyl, $C_7$-$C_{15}$phenylalkyl, cyclohexyl, $C_2$-$C_3$alkenyl.

Most preferred are compounds of formula I, IA, II, IIA, IV, IVA, VII, VIIA, VIII, VIIIA, IX, IXA, or the reaction product XI or XIA, especially those wherein k is 1 or 2; m is 2 or 3;

E is oxyl, hydroxyl, or $C_1$-$C_8$alkyl;

$R_1$, when n is 1, is H or $C_1$-$C_8$alkyl, or, when n is 2, is alkylene of 2-12 carbon atoms; and X is chloride, bromide or citrate.

The instant invention also pertains to a process for preventing the loss of brightness and for enhancing resistance to yellowing of a pulp or paper, particularly a chemimechanical or thermomechanical pulp or paper which still contain lignin, which comprises treating said pulp or paper with an effective stabilizing amount of a compound of any of formula I to XI or IA to XVIA as described above.

The effective stabilizing amount of the compounds of formula I to XVIA is 0.001 to 5% by weight based on the pulp or paper. Preferably, the effective stabilizing amount is 0.005 to 2% by weight; preferably 0.01 to 1% by weight.

When a coadditive stabilizer is also present, the effective stabilizing amount of the coadditives is also 0.001 to 5% by weight based on the pulp or paper; preferably 0.005 to 2% by weight; most preferably 0.01 to 2% by weight.

The instant compounds may additionally include an effective stabilizing amount of at least one stabilizer selected from the group consisting of the UV absorbers, the polymeric inhibitors, the sulfur containing inhibitors, the phosphorus containing compounds, the nitrones, the benzofuran-2-ones, fluorescent whitening agents, hindered amine hydroxylamines and salts thereof, hindered amine nitroxides and salts thereof, hindered amines and salts thereof, benzofuran-2-ones and metal chelating agents.

The compositions which also include a UV absorber are especially preferred. The UV absorber is selected from group consisting of the benzotriazoles, the s-triazines, the benzophenones, the α-cyanoacrylates, the oxanilides, the benzoxazinones, the benzoates and the α-alkyl cinnamates.

Preferably, the UV absorber is a benzotriazole, an s-triazine or a benzophenone, most especially a benzotriazole UV absorber or benzophenone UV absorber.

Typical and useful UV absorbers are, for example, 5-chloro-2-(2-hydroxy-3,5-di-ert-butylphenyl)-2H-benzotriazole;

2-(2-hydroxy-3,5-di-tert-butylphenyl)-2H-benzotriazole;

2-(2-hydroxy-3,5-di-tert-amylphenyl)-2H-benzotriazole;

2-(2-hydroxy-3,5-di-αcumylphenyl)-2H-benzotriazole;

2-(2-hydroxy-3-α-cumyl-5-tert-octylphenyl)-2H-benzotriazole;

2-(2-hydroxy-5-tert-octylphenyl)-2H-benzotriazole;

2-(2-hydroxy-3-tert-butyl-5-methylphenyl)-2H-benzotriazole-5-sulfonic acid, sodium salt;

3-tert-butyl-4-hydroxy-5-(2H-benzotriazol-2-yl)-hydrocinnamic acid;

12-hydroxy-3,6,9-trioxadodecyl 3-tert-butyl-4-hydroxy-5-(2H-benzotriazol-2-yl)-hydro-cinnamate;

octyl 3-tert-butyl-4-hydroxy-5-(2H-benzotriazol-2-yl)-hydrocinnamate;

4,6-bis(2,4-dimethylphenyl)-2-(4-(3-dodecyloxy*-2-hydroxypropoxy)-2-hydroxyphenyl)-s-triasine (*is mixture of $C_{12-14}$oxy isomers);

4,6-bis(2,4-dimethylphenyl)-2-(4-octyloxy-2-hydroxyphenyl)-s-triazine;

2,4-dihydroxybenzophenone;

2,2',4,4'-tetrahydroxy-5,5'-disulfobenzophenone, disodium salt;

2-hydroxy-4-octyloxybenzophenone;

2-hydroxy-4-dodecyloxybenzophenone;

2,4-dihydroxybenzophenone-5-sulfonic acid and salts thereof;

2-hydroxy-4-methoxybenzophenone-5-sulfonic acid and salts thereof;

2,2'-dihydroxy-4,4'dimethoxybenzophenone-5,5'-disodium sulfonate; and 3-(2H-benzotriazol-2-yl)-4-hydroxy-5-sec-butylbenzenesulfonic acid, sodium salt (CIBAFAS® W).

Other preferred compositions are those which additionally contain a polymeric inhibitor; preferably poly(ethylene glycol), poly(propylene glycol), poly(butylene glycol) or poly(vinyl pyrrolidone).

Still other preferred compositions wherein the additional stabilizer is a sulfur containing inhibitor; preferably polyethylene glycol dithiolacetate, polypropylene glycol dithiolacetate, polybutylene glycol dithioacetate, 1-thioglycerol, 2-mercaptoethyl ether, 2,2'thiodiethanol, 2,2'-dithiodiethanol, 2,2'oxydiethanethiol, ethylene glycol bisthioglycolate, 3-mercapto-1,2-propanediol, 2-(2-methoxyethoxy)-ethanethiol, glycol dimercaptoacetate, 3,3'-dithiopropionic acid, polyethylene glycol dithiol, polypropylene glycol dithiol, polybutylene glycol dithiol or ethylene glycol bis(mercaptoacetate).

Other preferred compositions are those wherein the additional stabilizer is a phosphorus containing compound; preferably tris(2,4-di-tert-butylphenyl)phosphite, 2,2',2"-nitrilo

[triethyl-tris(3,3',5,5'-tetra-tert-butyl-1,1'-biphenyl-2,2'-diyl)phosphite], bis(2,4-di-tert-butyl-6-methyl-phenyl) ethyl phosphite, sodium hydroxymethyl phosphinate, tetrakis(2,4-di-butylphenyl) 4,4'-biphenylenediphosphonite, tris(nonylphenyl)phosphite, bis(2,4-di-tert-butylphenyl) pentaerythrityl diphosphite, 2,2'-ethylidenebis(2,4-di-tert-butylphenyl) fluorophosphite or 2-butyl-2-ethylpropan-1,3diyl 2,4,6-tri-tert-butylphenyl phosphite.

Still other preferred compositions are those wherein the additional stabilizer is a benzo-furan-2-one; preferably 5,7-di-tert-butyl-3-(3,4-dimethylphenyl)-2H-benzofuran-2-one.

Still other preferred composition are those wherein the additional stabilizer is a metal chelating agent; preferably citric acid, keto acids, gluconates, heptagluconates, phosphates, phosphonates and aminocarboxylic acid chelates, such as ethylenediaminetetraacetic acid (EDTA), diethylenetriaminepentaacetic acid (DTPA), hydroxyethylethlenediaminetriacetic acid (HEDTA), nitrilotriacetic acid (NTA) and diethylenetriaminepentamethylenephosphonic acid (DTPMPA).

Some preferred compositions contain a mixture of additional stabilizers such as a mixture of a UV absorber and polymeric inhibitor; or a mixture of a UV absorber and a sulfur containing compound; or a mixture of a UV absorber and a phosphorus containing compound; or a mixture of a UV absorber and a metal chelating agent; or a mixture of a polymeric inhibitor and a sulfur containing compound; or a mixture of a polymeric inhibitor and a phosphorus containing compound; or a mixture of a sulfur containing compound and a phosphorus containing compound; or a mixture of a UV absorber, a polymeric inhibitor and a sulfur containing compound; or a mixture of a UV absorber, a polymeric inhibitor and a phosphorus containing compound; or a mixture of a UV absorber, a polymeric inhibitor, a sulfur containing compound and a phosphorus containing compound; or a mixture of a UV absorber, a polymeric inhibitor and a metal chelating agent.

Some preferred composition are those wherein the additional stabilizer is a mixture of a hindered amine hydroxylamine with at least one optical brightener such as 2,2'-[(1,1'-diphenyl)-4,4'-diyl-1,2-ethenediyl]bis-benzenesulfonic, disodium salt {or bis[4,4'-(2-stilbenesulfonic acid)], disodium salt} which is TINOPAL® SK, Ciba.

Preferably the compositions are those wherein the compound of formula I, II, III, IA, IIA or IIIA is of low molecular weight or contains hydrophilic moieties or is both of low molecular weight and contains hydrophilic moieties.

The instant inhibitor additive system can be added to pulp or paper at a number of places during the manufacturing or processing operations. These include
 a. on a pulp slurry in the latency chest;
 b. on a pulp slurry in or after the bleaching stage in a storage, blending or transfer chest;
 c. on pulp during or after bleaching, washing and dewatering followed by cylinder or flash drying;
 d. before or after the cleaners;
 e. before or after the fan pump to the paper machine headbox;
 f. to the paper machine white water;
 g. to the silo or save all;
 h. in the press section using a size press, coater or spray bar,
 i. in the drying section using a size press, coater or spray bar;
 j. on the calender using a wafer box;
 k. on paper in an off-machine coater or size press; and/or
 l. in the curl control unit.

Clearly, the precise location where the stabilizer additives should be added will depend on the specific equipment involved, the exact process conditions being used and the like. In some cases, the additives may be added at one or more locations for most effectiveness.

If the stabilizer or other coadditives are not themselves "water-soluble", they may be dispersed or emulsified by standard methods prior to application. Alternatively, the stabilizer and/or coadditives may be formulated into a paper sizing or paper coating formulation.

Stabilizers of present invention are also active as light stabilizers for organic materials, especially organic polymers. Thus, they may be appliad with advantage in bulk polymers such as polyolefins, films, fibers, or in coatings. Substrates, coadditives and specific ways of application for this purpose include those known in the art, e.g. as described in U.S. Pat. No. 5,948,836 column 3, line 37, until column 9, line 61 (substrates); col. 1, line 46, until col. 3, line 36, and col. 17, line 65, until col. 25, line 30 (coadditives); and col. 17, lines 39-61, col. 26, lines 33-39, and the same col. 26, line 52, until col. 27, line 18, and col. 28, lines 11-17 (methods of application).

The following examples are for illustrative purposes only and are not to be construed to limit the instant invention in any manner whatsoever.

Handsheet Treatment

All additives are applied by syringe-injecting the appropriate weight % of additive combination in either an aqueous solution when the additive is water soluble, or a solution in 1:1 ethanol/dioxane, onto bleached thermomechanical pulp (BTMP) brightness squares (4 cm×4 cm). The clamped sheets are allowed to air dry for one day.

The brightness of the handsheets is recorded before and after treatment by light exposure under controled intensity conditions.

Accelerated testing is carried out by subjecting the treated sheets to accelerated light induced yellowing in a fan-cooled light box containing eight fluorescent lamps with a spectral maximum output at 5700 Å with a total output approximately 43 times greater than normal office fluorescent lamps. The lamps are about ten inches away from the handsheets being illuminated.

Ambient testing is carried out by placing the treated handsheets on a desk under normal cool-white fluorescent office lights at a nominal distance of six feet.

In both cases, ISO brightness is tracked as a function of photolysis time and converted to post color number (PC number) in the usual manner.

Post color (PC) number is defined as follows:

$$PC = [(k/s)_{after} - (k/s)_{before}] \times 100$$

$$k/s = (1 - R_{inf})^2 / 2R_{inf}$$

where k and s are the absorption and scattering coefficients, respectively, and $R_{inf}$ is the value of ISO brightness.

The relationship between $R_{inf}$ and the chromophore concentration is non-linear, whereas, the PC number is roughly linearly related to the concentration of the chromophore in the sample.

Low PC numbers are desired as they indicate less yellowing.

When, using the ambient test conditions, untreated BTMP handsheets are compared to Kraft handsheets after 60 days, the BTMP handsheets have a PC number which is about 10 while the Kraft paper has a PC number which is about 0.39.

The Kraft handsheets are clearly less yellow than untreated BTMP handsheets after exposure to ambient light.

The incident light flux for the accelerated yellowing experiments (Examples 1-10) is 43 times greater than normal office fluorescent lamps as measured by the A. W. Speery SLM-110 digital light power meter. The brightness of the handsheets is tracked and compared to that of untreated sheets exposed in the same manner. The treated sheets exhibit significant resistance to yellowing as is seen below.

EXAMPLE 1

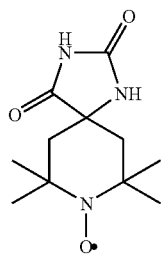

8-Oxyl-7,7,9,9-tetramethyl-1,3,8-triaza-spiro[4.5]decane-2,4-dione

The titled compound is synthesized by the procedure of L. Dulog and R. Seidemann, *Makromol. Chem.* 187, 2545 (1986).

EXAMPLE 2

8-Oxyl-7,7,9,9-tetramethyl-3-oxiranylmethyl-1,3,8-triaza-spiro[4.5]decane-2,4-dione To a solution of 2.0 g (8.3 mmol) of the compound of example 1 and 0.4 g (10 mmol) sodium hydroxide dissolved in 17 ml of water is added 0.92 g (10 mmol) epichlorohydrin. The reaction mixture is stirred at room temperature for 6 hrs. The mixture is partitioned between water and ethyl acetate. The organic phase is dried and concentrated. Purification by column chromatography yields the product as a red solid: mp 154° C.

EXAMPLE 3

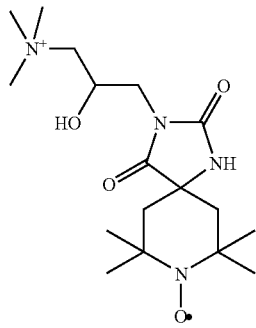

[2-Hydroxy-3-(8-oxyl-7,7,9,9-tetramethyl-2,4-dioxo-1,3,8-triaza-spiro[4.5]dec-3-yl)-prop]-trimethyl-ammonium chloride The compound in Example 2 is reacted with aqueous trimethylamine. One equivalent of hydrochloric acid is added to yield the titled compound.

EXAMPLE 4

N-Butyl-1-methoxy-2,2,6,6-tetramethyl-4-aminopiperidine

A 0.5 LParr hydrogenation bottle is charged with 10.3 g (55.6 mmol) of 1-methoxy-2,2,6,6-tetramethylpiperid-4-one, 8.0 g (110 mmol) n-butyl amine, 1.0 g 8% Pd, 2% Pt on carbon hydrogenation catalyst and 100 mL of isopropanol. The bottle is pressurized with 50 PSI of hydrogen and shaken for 4 hours. The catalyst is removed by filtration and the solvent and excess amine is removed by evaporation under reduced pressure. 11.0 g of the title compound is isolated as a colorless oil after column chromatography. $^1$H NMR (CDCL$_3$) δ 0.91 (t, 3 H), 1.12 (s, 6 H), 1.19 (s, 6 H), 1.25 (t, 2 H), 1.34 (m, 2H), 1.46 (q, 2 H), 1.73 (d, 2 H), 2.60 (t, 2 H), 2.77 (tt, 1 H), 3.60 (s, 3 H)

EXAMPLE 5

N-Butyl-N-(2-hydroxy-3-chloro)propyl-1-methoxy-2,2,6,6-tetramethyl-4-aminopiperidine A solution of 5.0 g (20.6 mmol) of N-butyl-1-methoxy-2,2,6,6-tetramethyl-4-aminopiperidine (Example 4) dissolved in 20 mL of epichlorohydrin is stirred for 48 hours at room temperature. The excess epichlorohydrin is removed by distillation and the title compound is isolated as a colorless oil after column chromatography. MS m/z 335 (M+H).

EXAMPLE 6

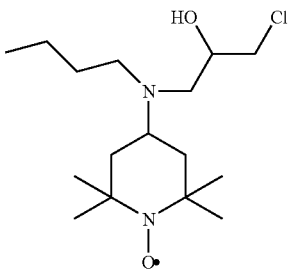

N-Butyl-N-(2-hydroxy-3-chloro)propyl-1-oxyl-2,2,6,6-tetramethyl-4-aminopiperidine The title compound is prepared according to the procedure of Example 5 by replacing N-butyl-1-methoxy-2,2,6,6-tetramethyl-4-aminopiperidine with N-butyl-1-oxyl-2,2,6,6-tetramethyl-4-aminopiperidine.

EXAMPLE 6A

N-Butyl-N-(2-hydroxy-3-chloro)propyl-1-hydroxy-2,2,6,6-tetramethyl-4-aminopiperidine The title compound is prepared according to the procedure of Example 5 by reaching N-butyl-1-methoxy-2,2,6,6-tetramethyl-4-aminopiperidine with N-butyl-1-hydroxy-2,2,6,6-tetramethyl-4-aminopiperdine.

EXAMPLE 7

N,N'-Bis-(2-hydroxy-3-chloro)propyl-N,N'-bis(1-oxyl-2,2,6,6-tetramethyl-piperidin-4-yl)-1,6-diaminohexane The title compound is prepared according to the method of Example 5 by replacing N-butyl-1-methoxy-2,2,6,6-tetramethyl-4-aminopiperidine with N,N'-bis(1-oxyl-2,2,6,6-tetramethylpiperidin-4-yl)-1,6-diaminohexane.

EXAMPLE 7A

N,N'-Bis-(2-hydroxy-3-chloro)propyl-N,N'-bis(1-hydroxy-2,2,6,6-tetramethyl-piperdin-4-yl)-1,6-diaminohexane The title compound is prepared according to the method of Example 5 by replacing N-butyl-1-methoxy-2,2,6,6-tetramethyl-4-aminopiperdine with N,N'-bis(1-hydroxy-2,2,6,6-tetramethyl-piperidin-4-yl)-1,6-diaminohexane.

EXAMPLE 8

1-Butyl-1-(1-methoxy-2,2,6,6-tetramethyl-piperidin-4-yl)-3-hydroxy-azetidinium Chloride The compound of Example 5 is heated at 100° C. in water for 2 hours to form the title compound as an equal mixture of diastereomers. $^1$H NMR (D$_2$O) δ 0.99 (t, 3 H), 1.25 (s, 3 H), 1.26 (s, 3 H), 1.35 (s, 6 H), 1.43 (m, 2 H), 1.68-1.84(m, 4 H), 2.03 (m, 2 H), 3.32 & 3.56 (t, 2 H), 3.64 & 3.83 (br t, 1 H), 3.70 (s, 3H), 4.13, 4.30, 4.50 & 4.70 (dd, 4 H), 4.71 & 4.84 (m, 1 H).

EXAMPLE 9

1-Butyl-1-(1-oxyl-2,2,6,6-tetramethyl-piperidin-4-yl)-3-hydroxy-azetidinium Chloride The compound of Example 6 is heated at 100° C. in water to form the title compound as an equal mixture of diastereomers. $^1$H NMR (CD$_3$OD) δ 0.98 (t, 3 H), 1.14 (s, 3 H), 1.15 (s, 3 H), 1.20 (s, 6 H), 1.39 (q, 2 H), 1.56-1.78 (m 4 H), 1.84-1.95 (m, 2 H), 3.20 & 3.44 (t, 2 H), 3.53 & 3.72 (br t, 1 H), 3.98, 4.15, 4.40, (dd, 3H), 4.53-4.72 (c, 2H). $^{13}$C NMR (CD$_3$OD) δ 69.8 (CH$_2$), 69.5 (CH$_2$), 59.3 (CH), 58.8 (CH), 38.5 (CH$_2$), 38.3 (CH$_2$), 32.8 (CH$_3$), 26.2 (CH$_2$), 25.9 (CH$_2$), 20.8 (CH$_2$), 20.0 (CH$_3$).

EXAMPLE 9A

1-Butyl-1-(1-hydroxy-2,2,6,6-tetramethyl-piperidin-4-yl)-3-hydroxy-azefidinium Chloride The compound of Example 6A is heated at 100° C. in water to form the title compound as an equal mixture of diastereomers.

EXAMPLE 10

N,N'-Bis(1-hydroxy-2,2,6,6-tetramethyl-piperidin-4-yl)-1,6-bis(3-hydroxyazetidinium)hexane The compound of Example 7A is heated at 100° C. in water to form the title compound.

EXAMPLE 11

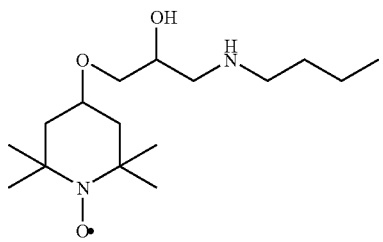

4-(3-Butylamino-2-hydroxy-propoxy)-2,2,6,6-tetramethyl-piperidin-1-oxyl

To a solution of 6.3 g (0.086 moles) n-butylamine dissolved in 50 mL of water is added 6.0 g (0.026 moles) 1-oxyl-2,2,6,6-tetramethyl-4-glycidyloxypiperidine (U.S. Pat. No. 6,080,864). The mixture is vigorously stirred for 24 hours and then partitioned between water and ethyl acetate. The organic phase is dried over sodium sulfate and concentrated under reduce pressure to yield the title compound as a red oil.

EXAMPLE 12

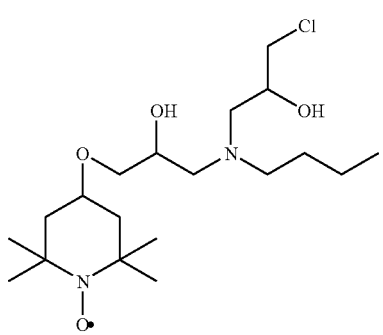

4-{3-[Butyl-(3-chloro-2-hydroxy-propyl)-amino]-2-hydroxy-propoxy}-2,2,6,6-tetramethyl-piperidin-1-oxyl The title compound is prepared according to the procedure of Example 5 by replacing N-butyl-1-methoxy-2,2,6,6-tetramethyl-4aminopiperidine with the compound of Example 11.

EXAMPLE 12A

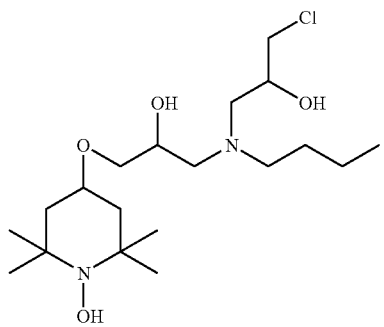

4-{3-[Butyl-(3-chloro-2-hydroxy-propyl)-amino]-2-hydroxy-propoxy}-2,2,6,6-tetramethyl-piperidin-1-ol The title compound is prepared according to the procedure of Example 5 by replacing N-butyl-1-methoxy-2,2,6,6-tetramethyl-4-aminopiperidine with 4-(3-Butylamino-2-hydroxy-propoxy)-2,2,6,6-tetramethyl-piperidin-1-ol

EXAMPLE 13

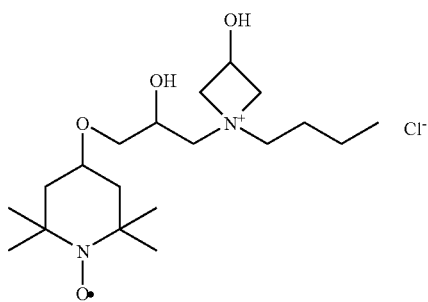

1-Butyl-3-hydroxy-1-[2-hydroxy-3-(1-oxyl-2,2,6,6-tetramethyl-piperidin-4-yloxy)-propyl]-azetidinium chloride The compound of Example 12 is heated at 100° C. in water to form the title compound.

EXAMPLE 13A

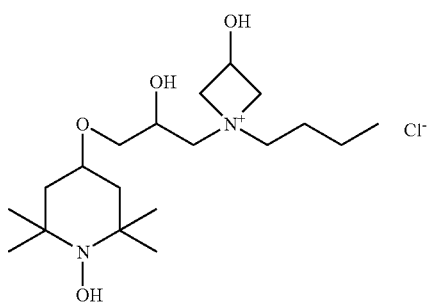

1-Butyl-3-hydroxy-1-[2-hydroxy-3-(1-hydroxy-2,2,6,6-tetramethyl-piperidin-4-yloxy)-propyl]-azetidinium chloride The compound of Example 12A is heated at 100° C. in water to form the title compound.

EXAMPLE 14

4-(2-Dimethylamino)ethoxy-1-oxyl-2,2,6,6-tetramethylpiperidine

To a two-phase mixture of 10 mL of 50% aqueous sodium hydroxide and 3 mL of toluene is added 0.26 g (0.8 mmol) of tetrabutylammonium bromide, 3.0 g (17.4 mmol) of 1-oxyl-4-hydroxy-2,2,6,6-tetramethylpiperidine and 2.5 g (17.4 mmol) of 2-dimethylaminoethyl chloride hydrochloride. The mixture is stirred vigorously at 70° C. for five hours. The reaction mixture is then partitioned between water and ethyl acetate. The organic phase is washed with water and dried over anhydrous sodium sulfate. Removal of the solvent leaves a red oil from which the title compound is isolated as a red oil by column chromatography.

EXAMPLE 15

4-(2-Dimethylamino)ethoxy-1-hydroxy-2,2,6,6-tetramethylpiperidine

A 0.5 L Parr bottle is charged with 2.0 g (8.2 mmol) 4-(2-Dimethylamino)ethoxy-1-oxyl-2,2,6,6-tetramethylpiperidine (Example 14), 100 mg 5% Pt on C hydrogenation catalyst and 100 mL of methanol. The bottle is pressurized to 50 psi with hydrogen and shaken for 30 minutes. The catalyst is removed by filtration and the methanol is removed by evaporation under reduced pressure to yield the titled compound as a pale yellow viscous oil. $^1$H NMR (CDCL$_3$) δ 1.15 (s, 6 H), 1.20 (s, 6 H), 1.45 (t, 2 H), 1.92 (d, 2 H), 2.41 (s, 6 H), 2.65 (t, 2 H), 3.59 (tt, 1 H), 3.64 (t, 2 H)

EXAMPLE 16

4-(2-Dimethylpropylammonium)ethoxy-1-oxyl-2,2,6,6-tetramethylpiperidine bromide

A solution of 5.0 g (20.5 mmol) of 4-(2-Dimethylamino)ethoxy-1-oxyl-2,2,6,6-tetramethylpiperidine (Example 14) and 5.05 g (41 mmol) propyl bromide dissolved in 25 mL of ethanol is refluxed for 3 hours. The solvent is evaporated under reduced pressure, the residue is washed with ethyl acetate and then dried under vacuum to yield 6.5 g of the product as a red oil. MS-FAB m/z 287 (M ion minus Br and plus H)

EXAMPLE 17

4-(2-Dimethylpropylammonium)ethoxy-1-hydroxy-2,2,6,6-tetramethylpiperidine bromide The title compound is prepared according to the procedure of Example 15 by replacing 4-(2-Dimethylamino)ethoxy-1-- oxyl-2,2,6,6-tetramethylpiperidine with 4-(2-Dimethylporpylammonium)ethoxy-1-oxyl-2,2,6,6-tetramethypiperdine bromide. A pale yellow viscous oil is obtained. $^1$H NMR (CD$_3$OH) δ 0.99 (t, 3 H), 1.15 (s, 6 H), 1.18 (s, 6 H), 1.41 (t, 2 H), 1.80 (m, 2 H), 1.95 (d, 2 H), 3.11 (s, 6 H), 3.31 (m, 2 H), 3.52 (br t, 2 H), 3.71 (tt, 1 H), 3.87 (br m,2 H)

EXAMPLE 18

N,N ,N',N'-Tetramethyl-N,N'-bis-[3-(1-oxyl-2,2,6,6-tetramethylpipeddin-4-yloxy)-propyl]-hexamethylenediammonium Dibromide The title compound is prepared according to the procedure of Example 16 by replacing propyl bromide with 1,6-dibromohexane. A red oil is obtained. MS-FAB m/z 651 (M ion minus Br and plus 2 H)

EXAMPLE 19

1,7-Bis-(1-hydroxy-2,2,6,6-tetramethylpiperidin4-yl) 1,4,7-triazaheptane

A Parr shaker bottle containing 20.0 g (0.117 mol) 1-oxyl-2,2,6,6-tetramethylpiperidin-4-one, 6.0 g (0.058 mol) diethylenetriamine, 0.5 g 8% Pt/2% Pd on Carbon and 120 mL methanol is pressurized with hydrogen and shaken for 2 hours. The catalyst is removed by filtration and the solution is concentrated to 40 mL. The product is precipitates as a white solid with the addition of 200 mL of ethyl ether: mp 118-124° C.

EXAMPLE 20

The compound of Example 19 is reacted with one to four equivalents of 2,3-epoxypropyl-trimethylammonium chloride to yield a water soluble hydroxylamine.

EXAMPLE 21

Accelerated Yellowing with High Intensity Lamps

A sheet consisting of 75% bleached mechanical fibers and 25% bleached kraft is treated with 1.0% by weight of a test compound from Examples 14, 15, 16 and 17 and exposed to accelerated aging as described above. The sheets treated with these novel additives exhibit substantial inhibition of yellowing compared to the untreated control sheet.

EXAMPLE 22

Accelerated Yellowing with High Intensity Lamps

A sheet consisting of 75% bleached mechanical fibers and 25% bleached kraft is treated with 1.0% by weight of a test compound from Examples 14, 15, 16 and 17 and 0.5% by weight of Cibafast W, a UV absorber. The sheets treated with these novel additives and a UV absorber exhibit substantial inhibition to yellowing compared to the untreated control sheet and illustrate the performance enhancement when a combination of instant compound with a UV absorber is used.

EXAMPLE 23

Accelerated Yellowing with High Intensity Lamps

A BTMP sheet is treated with 1.0% by weight of a test compound from Examples 14, 15, 16 and 17 and 0.5% by weight of citric acid, a metal chelabng agent. The sheets treated with these novel polymeric additive materials and a metal chelating agent exhibit substantial inhibition to yellowing compared to the untreated control sheet and illustrate the performance enhancement when a combination of instant compound with a metal chelating agent is used.

EXAMPLE 24

Accelerated Yellowing with High Intensity Lamps

A BTMP sheet is treated with 1.0% by weight of a test compound from Examples 3 to 20 and 0.5% by weight of a UV absorber. The sheets treated with these novel polymeric additive materials and a UV absorber exhibit substantial inhibition to yellowing compared to the untreated control sheet and illustrate the performance enhancement when a combination of instant compound with a UV absorber is used.

EXAMPLE 25

Accelerated Yellowing with High Intensity Lamps

A BTMP sheet is treated with 1.0% by weight of a test compound from Examples 3 to 20 and 0.5% by weight of a metal chelabng agent The sheets treated with these novel polymeric additive materials and a metal chelating agent exhibit substantial inhibition to yellowing compared to the untreated control sheet and illustrate the performance enhancement when a combination of instant compound with a metal chelating agent is used.

EXAMPLE 26

Accelerated Yellowing with High Intensity Lamps

A BTMP sheet is treated with 1.0% by weight of a test compound from Examples 3 to 20 and 0.5% by weight of a fluorescent whitening agent. The sheets treated with these novel polymeric additive materials and a fluorescent whitening agent exhibit substantial inhibition to yellowing compared to the untreated control sheet and illustrate the performance enhancement when a combination of instant compound with a fluorescent whitening agent is used.

What is claimed is:

1. A compound of any of formulas IX, IXA, X or XA where
    n is 1 or 2; and m ranges from 2 to 6;
    E is oxyl, hydroxyl, hydrogen, alkyl, alkyl substituted by hydroxyl, by oxo or by carboxy, alkyl interrupted by oxygen, by —COO— or by —OCO—, alkenyl, alkynyl, cycloalkyl, cycloalkenyl, bicycloalkyl, alkoxy, alkoxy substituted by hydroxyl, by oxo or by carboxy, alkoxy interrupted by oxygen, by —COO— or by —OCO—, cycloalkoxy, alkenyloxy, cycloalkenyloxy, aralkyl, aralkoxy, acyl, RCO0—, ROCOO—, RNCOO— or chloro where R is an aliphatic or aromatic moiety, when n is 1, R₁ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, alkyl of 2 to 50 carbon atoms substituted by one to ten hydroxyl groups or both interrupted by said oxygen atoms and substituted by said hydroxyl groups, or R₁ is alkyl of 1 to 4 carbon atoms substituted by a carboxy group or by —COOZ where Z is hydrogen, alkyl of 1 to 4 carbon atoms or phenyl, or where Z is said alkyl substituted by —(COO⁻)$_n$M$^{n+}$ where n is 1-3 and M is a metal ion from the 1st, 2nd or 3rd group of the periodic table or is Zn, Cu, Ni or Co, or M is a group N$^{n+}$(R₂)₄ where R₂ is hydrogen, alkyl of 1 to 8 carbon atoms or benzyl, or when n is 2, R₁ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, X is an inorganic or organic anion, where the index j in formulae IX to XA equals the number of ammonium ions in the formula divided by the valency of X; and the total charge of cations is equal to the total charge of anions.

2. A compound according to claim 1 wherein the anion X is phosphate, phosphonate, carbonate, bicarbonate, nitrate, chloride, bromide, iodide bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenediaminetetraacetic acid or of diethylenetriaminepentaacetic acid, an alkylsulfonate or an arylsulfonate.

3. A compound according to claim 1 wherein E is selected from oxyl, hydroxyl, C₁-C₁₈alkoxy; C₃-C₁₈alkoxy substituted by hydroxyl, oxo or carboxy or interrupted by oxygen or carboxy; C₅-C₁₂cycloalkoxy; C₃-C₁₂alkenyloxy; cyclohexenyloxy; aralkyl or aralkoxy of 7 to 15 carbon atoms; C₁-C₁₂acyl; R(C=O)O—, RO(C=O)O—, RN(C=O)O—, where R is C₁-C₁₈alkyl, phenyl, C₇-C₁₅phenylalkyl, cyclohexyl, C₂-C₃alkenyl.

4. A compound according to claim 1 of formula IX or IXA.

5. A compound according to claim 1, wherein m is 2 or 3;

E is oxyl, hydroxyl, or C₁-C₈alkyl;

R₁, when n is 1, is H or C₁-C₈alkyl, or, when n is 2, is alkylene of 2-12 carbon atoms; and X is chloride, bromide or citrate.

* * * * *